United States Patent
Vitello et al.

(10) Patent No.: US 10,898,659 B1
(45) Date of Patent: Jan. 26, 2021

(54) SYSTEM FOR HANDLING AND DISPENSING A PLURALITY OF PRODUCTS

(71) Applicants: Patrick Vitello, Pompano Beach, FL (US); Robert Banik, Ft. Lauderdale, FL (US); Timothy Brandon Hunt, Hollywood, FL (US)

(72) Inventors: Patrick Vitello, Pompano Beach, FL (US); Robert Banik, Ft. Lauderdale, FL (US); Timothy Brandon Hunt, Hollywood, FL (US)

(73) Assignee: International Medical Industries Inc., Pompano Beach, FL (US)

( * ) Notice: Subject to any disclaimer, the term of this patent is extended or adjusted under 35 U.S.C. 154(b) by 117 days.

(21) Appl. No.: 15/985,528

(22) Filed: May 21, 2018

Related U.S. Application Data (60) Provisional application No. 62/508,674, filed on May 19, 2017.

(51) Int. Cl.
| | |
|---|---|
| *A61M 5/50* | (2006.01) |
| *A61J 1/20* | (2006.01) |
| *A61M 5/32* | (2006.01) |
| *A61M 5/31* | (2006.01) |
| *A61J 1/14* | (2006.01) |

(52) U.S. Cl.
CPC .............. *A61M 5/50* (2013.01); *A61J 1/2096* (2013.01); *A61M 5/3134* (2013.01); *A61M 5/3202* (2013.01); *A61J 1/1406* (2013.01); *A61M 2005/3103* (2013.01)

(58) Field of Classification Search
CPC .... A61M 5/50; A61M 5/3134; A61M 5/3202; A61J 1/2096; A61J 1/1406
USPC .... 206/535–537, 528, 223; 221/67, 68, 151, 221/152, 287
See application file for complete search history.

(56) References Cited

U.S. PATENT DOCUMENTS

| | | |
|---|---|---|
| 732,662 A | 6/1903 | Smith |
| 1,678,991 A | 7/1928 | Marschalek |
| 1,970,631 A | 8/1934 | Sherman |
| 2,477,598 A | 8/1949 | Hain |

(Continued)

FOREIGN PATENT DOCUMENTS

| | | |
|---|---|---|
| EP | 0148116 A | 7/1985 |
| WO | WO 2008/000279 | 1/2008 |
| WO | WO 2017086607 | 5/2015 |

*Primary Examiner* — Rafael A Ortiz
(74) *Attorney, Agent, or Firm* — Malloy & Malloy, PL; Jennie S. Malloy (57) ABSTRACT

A system for handling and dispensing a plurality of products, including a package having a chamber configured to contain the plurality of products in a predetermined aligned relation to one another and a base disposed in surrounding relation to said chamber. A retaining structure is disposed within an interior of the base in retaining relation with the plurality of products and an access device is disposable in opening engagement with the retaining structure and in accessible relation with an interior of the chamber and the plurality of products therein. The access device comprises a path of travel of the plurality of products out of said chamber when disposed in opening relation to the retaining structure and is structured to assume an interface orientation wherein said access device is disposed in interconnected relation between the package and a dispensing assembly.

10 Claims, 8 Drawing Sheets

(56) References Cited

U.S. PATENT DOCUMENTS

| | | |
|---|---|---|
| 2,739,590 A | 3/1956 | Yochem |
| 2,823,674 A | 2/1958 | Yochem |
| 2,834,346 A | 5/1958 | Adams |
| 2,875,761 A | 3/1959 | Helmer et al. |
| 2,888,015 A | 5/1959 | Hunt |
| 2,952,255 A | 9/1960 | Hein, Jr. |
| 3,122,280 A | 2/1964 | Goda |
| 3,245,567 A | 4/1966 | Knight |
| 3,323,798 A | 6/1967 | Miller |
| 3,364,890 A | 1/1968 | Andersen |
| 3,368,673 A | 2/1968 | Cowley |
| 3,598,120 A | 8/1971 | Mass |
| 3,610,241 A | 10/1971 | LeMarie |
| 3,700,215 A | 10/1972 | Hardman et al. |
| 3,706,307 A | 12/1972 | Hasson |
| 3,712,749 A | 1/1973 | Roberts |
| 3,747,751 A | 7/1973 | Miller et al. |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klein et al. |
| 4,589,171 A | 5/1986 | McGill |
| 4,664,259 A | 5/1987 | Landis |
| 4,667,837 A | 5/1987 | Vitello et al. |
| 4,676,530 A | 6/1987 | Nordgren et al. |
| 4,693,707 A | 9/1987 | Dye |
| 4,726,483 A | 2/1988 | Drozd |
| 4,743,229 A | 5/1988 | Chu |
| 4,743,231 A | 5/1988 | Kay et al. |
| 4,760,847 A | 8/1988 | Vaillancourt |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,049,129 A | 9/1991 | Zdeb et al. |
| 5,057,093 A | 10/1991 | Clegg et al. |
| D323,392 S | 1/1992 | Byrne |
| 5,135,496 A | 8/1992 | Vetter et al. |
| 5,165,560 A | 11/1992 | Enniss, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Denmark |
| 5,328,474 A | 7/1994 | Raines |
| 5,356,380 A | 10/1994 | Hoekwater et al. |
| 5,380,295 A | 1/1995 | Vacca |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,617,954 A * | 4/1997 | Kato .................... G03D 3/065 206/528 |
| 5,624,402 A | 4/1997 | Imbert |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Liff et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| 5,829,589 A * | 11/1998 | Nguyen ................ A61M 5/002 206/366 |
| D402,766 S | 12/1998 | Smith et al. |
| 5,883,806 A | 3/1999 | Meador et al. |
| 5,884,457 A | 3/1999 | Ortiz et al. |
| 5,902,269 A | 5/1999 | Jentzen |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsals |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,375,640 B1 | 4/2002 | Teraoka |
| 6,394,983 B1 | 5/2002 | Mayoral et al. |
| 6,485,460 B2 | 11/2002 | Eakins et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanley et al. |
| 6,755,220 B2 | 6/2004 | Castellano et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,935,560 B2 | 8/2005 | Andreasson et al. |
| 6,942,643 B2 | 9/2005 | Eakins et al. |
| 7,055,273 B2 | 6/2006 | Roshkoff |
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |

(56) References Cited

U.S. PATENT DOCUMENTS

| | | |
|---|---|---|
| 7,232,066 B2 | 6/2007 | Andreasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| 7,482,166 B2 | 1/2009 | Nollert et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,918,830 B2 | 4/2011 | Langan et al. |
| 7,922,213 B2 | 4/2011 | Werth |
| 8,034,041 B2 | 10/2011 | Domkowski |
| 8,079,518 B2 | 12/2011 | Turner et al. |
| 8,091,727 B2 | 1/2012 | Domkowski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B2 | 1/2013 | Vitello |
| 8,353,869 B2 | 1/2013 | Ranalletta et al. |
| 8,443,999 B1 | 5/2013 | Reinders |
| D684,057 S | 6/2013 | Kwon |
| 8,512,277 B2 | 8/2013 | Del Vecchio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,082,157 B2 | 7/2015 | Gibson |
| 9,101,534 B2 | 8/2015 | Bochenko |
| D738,495 S | 9/2015 | Strong et al. |
| D743,019 S | 11/2015 | Schultz |
| 9,199,042 B2 | 12/2015 | Farrar et al. |
| 9,199,749 B1 | 12/2015 | Vitello |
| 9,220,486 B2 | 12/2015 | Schweiss et al. |
| 9,220,577 B2 | 12/2015 | Jessop et al. |
| 9,227,019 B2 | 1/2016 | Swift et al. |
| D750,228 S | 2/2016 | Strong et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S | 6/2016 | Ingram et al. |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Insgram et al. |
| D777,903 S | 3/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello et al. |
| D815,945 S | 4/2018 | Fischer |
| 9,987,438 B2 | 6/2018 | Stillson |
| D825,746 S | 8/2018 | Davis et al. |
| 10,039,913 B2 | 8/2018 | Yeh |
| D831,201 S | 10/2018 | Holtz et al. |
| D820,187 S | 11/2018 | Ryan |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,376,655 B2 | 8/2019 | Pupke et al. |
| D859,125 S | 9/2019 | Weagle et al. |
| 10,758,684 B1 | 9/2020 | Vitello et al. |
| 2001/0003150 A1 | 6/2001 | Imbert |
| 2001/0034506 A1 | 10/2001 | Hirschman et al. |
| 2001/0056258 A1 | 12/2001 | Evans |
| 2002/0007147 A1 | 1/2002 | Capes et al. |
| 2002/0023409 A1 | 2/2002 | Py |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0133119 A1 | 9/2002 | Eakins et al. |
| 2003/0055685 A1 | 3/2003 | Cobb et al. |
| 2003/0146617 A1 | 8/2003 | Franko, Sr. |
| 2003/0183547 A1 | 10/2003 | Heyman |
| 2004/0008123 A1 | 1/2004 | Carrender et al. |
| 2004/0064095 A1 | 4/2004 | Vitello |
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1 | 4/2008 | Buehler et al. |
| 2008/0106388 A1 | 5/2008 | Knight |
| 2008/0140020 A1 | 6/2008 | Shirley |
| 2008/0243088 A1 | 10/2008 | Evans |
| 2008/0306443 A1 | 12/2008 | Neer |
| 2009/0084804 A1 | 4/2009 | Caspary |
| 2009/0099552 A1 | 4/2009 | Levy et al. |
| 2009/0149815 A1 | 6/2009 | Kiel et al. |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |

(56) References Cited

U.S. PATENT DOCUMENTS

| | | |
|---|---|---|
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin et al. |
| 2014/0353196 A1 | 12/2014 | Key |
| 2015/0182686 A1 | 7/2015 | Okihara |
| 2015/0191633 A1 | 7/2015 | De Boer et al. |
| 2015/0305982 A1 | 10/2015 | Bochenko |
| 2015/0310771 A1 | 10/2015 | Atkinson et al. |
| 2016/0067422 A1 | 3/2016 | Davis et al. |
| 2016/0090456 A1 | 3/2016 | Ishimaru et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Vitello et al. |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1 | 1/2017 | Duinat et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0319438 A1 | 11/2017 | Davis et al. |
| 2017/0354792 A1 | 12/2017 | Ward |
| 2018/0001540 A1 | 1/2018 | Byun |
| 2018/0078684 A1 | 3/2018 | Peng et al. |
| 2018/0089593 A1 | 3/2018 | Patel et al. |

\* cited by examiner

SYSTEM FOR HANDLING AND DISPENSING A PLURALITY OF PRODUCTS

CLAIM OF PRIORITY

The present application is based on and a claim of priority is made under 35 U.S.C. Section 119(e) to a provisional patent application.

BACKGROUND OF THE INVENTION

Field of the Invention

This invention relates to a system for at least partially automating the handling and dispensing of a plurality of products, which may include tamper evident closures, in a sterile manner. Sterility of the closures/products environment is at least partially maintained by eliminating or significantly reducing the possibility of touching or the need to manually touch the closures/products during the handling, dispensing or other processing thereof.

Description of the Related Art

In the medical field, it is a relatively common for authorized medical personnel to prescribe a drug or medication for a patient which is to be given by injection or other procedures, such as administering fluids to the patient by intravenous (IV) infusion. It is also relatively common procedure for syringes and other drug administering devices to be pre-loaded or filled by pharmacists or other authorized personnel, whether within the hospital or at another facility and location, at what may be generally referred to as a filling station. However, a filling station is typically located in a remote part of the hospital or other facility, relative to the patient care area where the injection is to be administered. Indeed, at large medical facilities, a filling station may resemble a factory on the hospital grounds from which drugs and other fluids are delivered to multiple nursing stations at different locations. Because of the remote location of many nurse's stations relative to a filling station, a fluid or drug loaded administering device is very often given to another person for delivery to a nurse's station for subsequent dosing of the patient by a duly qualified nurse or other medically trained person. As a result, a pre-loaded syringe may travel quite some distance and be handled by several people before it reaches a nurse's station, which raises some concern that the contents of the syringe may be tampered with or cause the sterility of the syringe and/or its contents to be comprises.

Additionally, in the case where a drug has been prescribed that is a very expensive or addictive, such as but not limited to morphine, has been pre-loaded in the syringe or other administering device, there is a danger that the pre-loaded syringe or other administering device will be tampered with at some point, by a person seeking unauthorized access to the drug. This possibility can present a real danger if such a person were to gain access to the prescribed medicine and then, inappropriately and without concern, substitute some other, unauthorized material in the syringe which looks like the actual prescribed medicine and dosage. By way of an example only, if saline solution or water or another drug were substituted for a dose of morphine, the patient would not receive the prescribed drug which by itself, could be quite harmful, while the substituted content might potentially also cause serious harm. Thus, there is a problem of knowing if a sealed, pre-loaded syringe or other administering device has, or has not, been exposed to contamination or might otherwise have been compromised by its being tampered with. This and related types of problems have been described in one or more previously issued U.S. patents owned by the Applicant/Assignee herein, such as U.S. Pat. No. 5,328,474.

More specifically, and in order to overcome the disadvantages and concerns associated with the growing use of syringes and/or other medical devices that are pre-filled with various prescribed medicines, the Applicant/Assignee herein has developed a variety of "tamper evident structures". Such tamper evident structures or assemblies are structured to prevent or at least restrict access to the contents of a pre-filled syringe. If in fact, access has been accomplished or even attempted to a pre-filled syringe or other drug administering device, such tamper evident assemblies are intended to provide a clear indication of having been tampered with.

In the field relating to closures for medical devices, it is well known that packaging, dispensing, installation, etc. of such tamper evident closures is preferably done in a relatively sterile environment. Therefore, during such processing of medical closures, it is important to maintain a degree of sterility. This is due at least in part to the fact that such tamper evident closures may be attached in closing/sealing relation to a prefilled syringe or other type medical container having medicine or other fluids retained therein. Because the retained medicines and/or fluids are typically intended to be administered to a patient, sterility of the closure may be an important factor.

As such, there is a need in this field of art for a system that eliminates or significantly reduces the need to handle or manually touch one or more closures, while the closures are being dispensed from a packaging to another device, piece of machinery or equipment, which is used to facilitate the installation or other processing of the closures. It would also be helpful if any such system were developed to allow for at least partial automation, thereby further diminishing the need to manually touch or handle the closures, while dispensing the one or more closures from the packaging in an efficient manner. Also, in order to enhance the operational versatility of any such system that were developed, it would further be desirable to operatively interconnect the package of one or more closures to a delivery/processing assembly, thereby further facilitating automated dispensing of the closures.

SUMMARY OF THE INVENTION

The present invention is intended to present a solution to the foregoing and other needs which remain in this field of art, and as such, is directed to a system which is operable to maintain and enhance the sterility of a plurality of products during their processing and more specifically, wherein the plurality of products are automatically removed from a package and dispensed, in a substantially automated manner, to a delivery/processing assembly.

It will be noted that the system, as well as the attendant structural components and operative features associated therewith, may be described in relation to the handling and dispensing of a plurality of tamper evident closures. However, it is emphasized that the system, including the different structural embodiments associated with the practice thereof, is adaptable for use with the handling of a plurality of products, other than tamper evident closures. Moreover, the system of the present invention is specifically, but not exclusively adapted to facilitate the handling, dispensing, etc. of a plurality of products in a manner which eliminates or significantly reduces the need and/or possibility of touching or manually handling the plurality of products while being processed. As a result, at least a certain degree of sterility, if not full sterility, may be maintained due to the automated features incorporated within the system of the present invention.

In more specific terms, the system of the present invention comprises the utilization of a package which includes a chamber configured to contain the "plurality of products" in a predetermined aligned relation to one another. As indicated hereinafter, such an aligned relation of the plurality of retained products will facilitate their automated removal from the package, as well as their dispensing to an intended delivery/processing facility, machine, device, etc. Moreover, the package includes a base disposed in at least partially surrounding relation to the chamber, and structured to restrict manual access to the chamber, as well as the plurality of products contained therein.

Additional features of one or more embodiments of the package include a retaining structure disposed on the base in retaining relation with the plurality of products, so as to at least initially restrict their passage from the chamber to an exterior thereof. In order to further restrict access to the plurality of products in the chamber, the retaining structure is disposed at least partially within an interior of the base, such as in an interior recessed portion thereof, which is not readily accessible by the hand, finger, etc. of an individual.

The system of the present invention also includes an access device that is disposed and structured to facilitate an opening of the package, concurrent to providing access to the plurality of products therein. In addition, the access device has an open interior structured to at least partially define a "path of travel" of the plurality of products from the interior of the chamber to an exterior thereof.

Accordingly, the access device is dimensioned and configured to assume an "interface orientation" and to serve as an interface between the package, the plurality of products contained therein and the aforementioned delivery/processing assembly, to which the plurality of products are dispensed. Therefore, the access device/interface is cooperatively structured with both the packaging, in which the plurality of products are initially retained in a sterile environment, and the delivery/processing assembly to which the plurality of products are automatically delivered. In more specific terms, the interface orientation of the access device further comprises the chamber, a path of travel defined by an open interior of the access device and the plurality of products all being collectively disposed in a vertical alignment with the delivery/processing assembly. This preferred vertical alignment facilitates a gravity influenced passage of the plurality of products through the path of travel on the interior the access device and to the receiving portion of the delivery/processing assembly.

As set forth above, the packaging also includes a retaining structure disposed within a recessed interior of the base in order to render manual access to the chamber and the plurality of products contained therein more difficult. Moreover, one or more preferred embodiments of the package of the system of the present invention may include a pocket formed in the base, wherein the pocket includes at least one open end. The open end is disposed in communicating relation with an outer periphery of the base and/or an exterior of the package.

In cooperation therewith, the aforementioned access device includes a penetrating portion structured to assume an operative orientation. The operative orientation of the penetrating portion may be at least generally defined by disposition of the penetrating portion within the interior of the package in opening engagement or relation to the retaining portion. Such opening engagement will result in an opening of the chamber and a passage of the plurality of products retained therein preferably, but not necessarily, under the influence of gravity.

The versatility of the system of the present invention may be enhanced by varying the structure and operative features of the package in which the plurality of products are initially and removably retained. Accordingly, one preferred embodiment of the system comprises the packaging formed of an at least partially flexible base disposed in surrounding, access restricting relation to the chamber. In cooperation therewith, the chamber may have a "blister-like" construction.

Yet another embodiment of the packaging, associated with the system of the present invention, is distinguishable in structure but at least partially similar in operation. As such, the additional preferred embodiment of the package includes a rigid base having an elongated, substantially tubular structure, wherein the aforementioned chamber is disposed within the interior of the tubular base and extends along the length thereof.

Common to both of the above noted embodiments of the package is the disposition of the retaining structure at least partially within the base of the package. More specifically, each of the packages include a pocket having an open end, wherein the corresponding retaining structures are disposed within the pocket for purposes of reducing the possibility of manual access thereto.

Additional features common to one or more preferred package embodiments include the cooperative structuring of corresponding access devices to be used with the different embodiments of the packages. As such, the different access devices may be further structured to assume the aforementioned interface orientation and thereby effectively serve as an interface between the different packages and the delivery/processing assembly to which the plurality of products are dispensed. It should be apparent that due to a variance in the structure of the different packages, there will be a cooperative variance in the structure of the corresponding access device/interface.

However, common to each of the one or more possible access devices, is the inclusion of an open, at least partially hollow interior that defines a path of travel there-through. As a result, when the access device is in the interface orientation, in interconnecting relation between an open package and the delivery/processing assembly to which the plurality of products are being dispensed, passage of the plurality of products from the package, through the access device and to the delivery/processing assembly is significantly facilitated, preferably under the influence of gravity.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

The present invention is directed to a system for the handling and dispensing of a plurality of products in a manner which avoids the physical touching of the products, in an attempt to maintain a sterile condition thereof. It will be noted that the structural and operative features of the present system will be described, at least in part, with reference to a plurality of tamper evident closures (TEC). Due to the environment of the invention being in the medical art, the packaging, dispensing, and installation of such tamper evident closures is preferably done in a clean or sterile environment.

This is due at least in part to the fact that such tamper evident closures may be attached in closing/sealing relation to a pre-filled syringe or other type of medical container having a prescribed drug, medicine or other fluids retained therein. Because the retained medicines and/or fluids are typically intended to be administered to a patient, sterility of the syringe, medical container and closure will typically be important. Accordingly, the system of the present invention handles, dispenses, and otherwise processes a plurality of closures in a manner which facilitates the ability to maintain the closures as sterile. As set forth above, this is accomplished, at least in part, by eliminating or significantly reducing the possibility of or need to manually handle and/or touch the individual closures, during the processing procedure associated with the system of the present invention. Accordingly, the structural and operative features of the various preferred embodiments of the system of the present invention is at least partially automated.

It is also emphasized that the system of the present invention is specifically adaptable for use with the processing of the tamper evident closures, as generally set forth herein. However, the system, including the attendant structural components associated therewith, are also equally adaptable for the processing of a "plurality of products," other than tamper evident closures or other medical closures of the type associated with pre-filled syringes, medical containers, etc.

Figure 1:
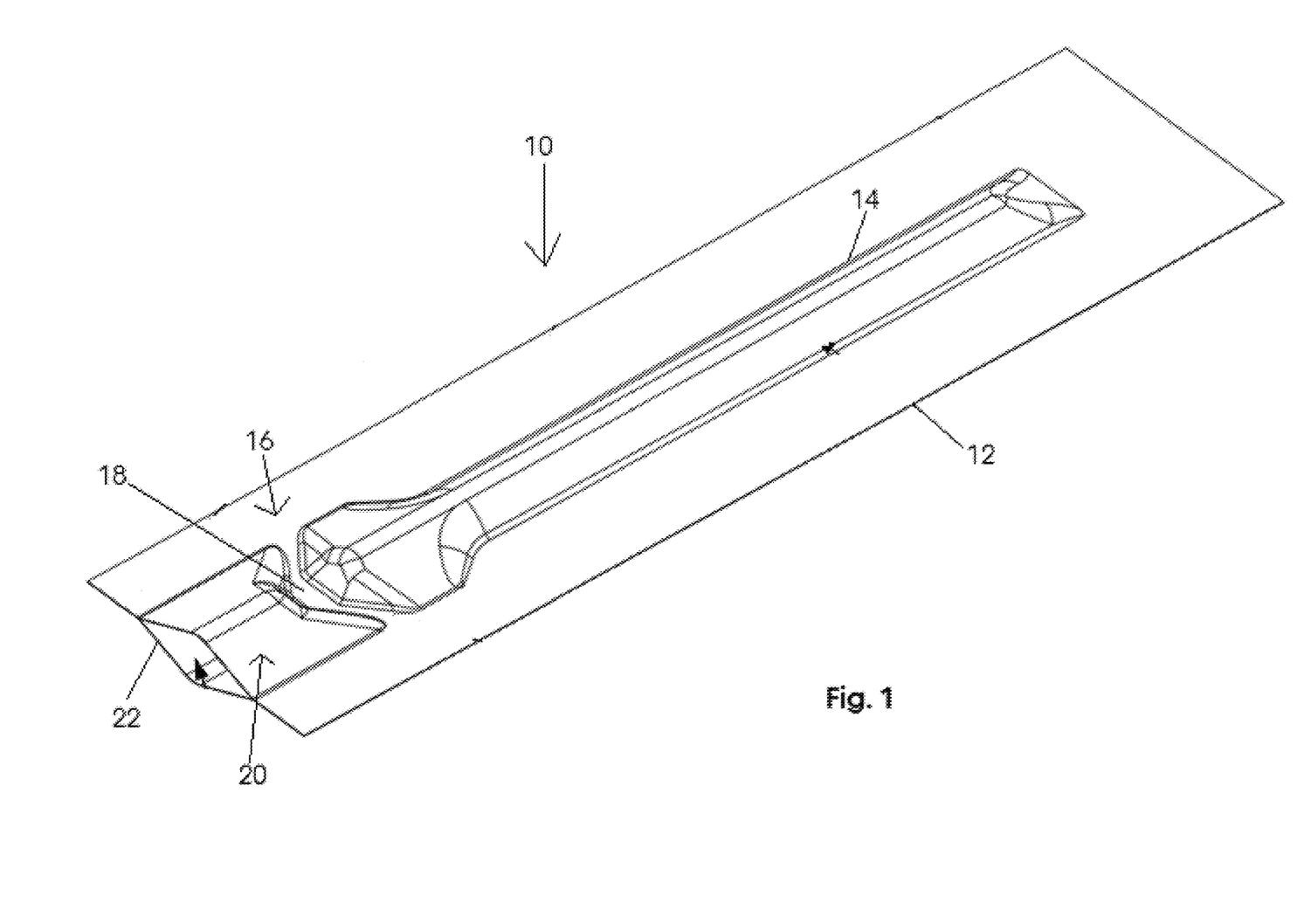
FIG. 1 is a perspective view of one preferred embodiment of a package associated with the handling and dispensing system of the present invention.
Figure 2A:
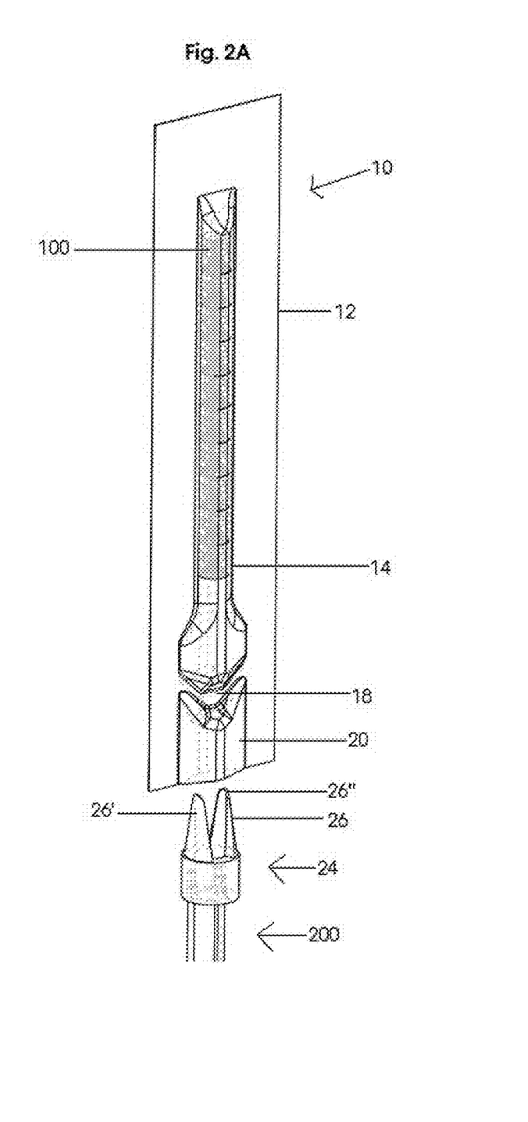
FIG. 2A is a perspective view of the package of the embodiment of FIG. 1 and an access device for opening the package to facilitate access to the contents thereof.
Figure 2B:
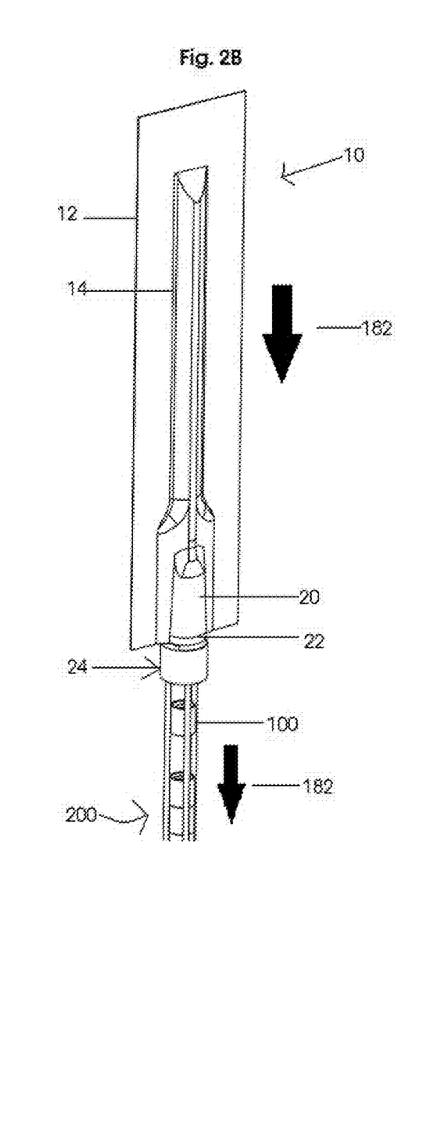
FIG. 2B is a perspective view of the package and access device illustrated in FIG. 2A, but wherein the access device is disposed in an interfacing orientation between the package and a dispensing assembly.
Figure 3:
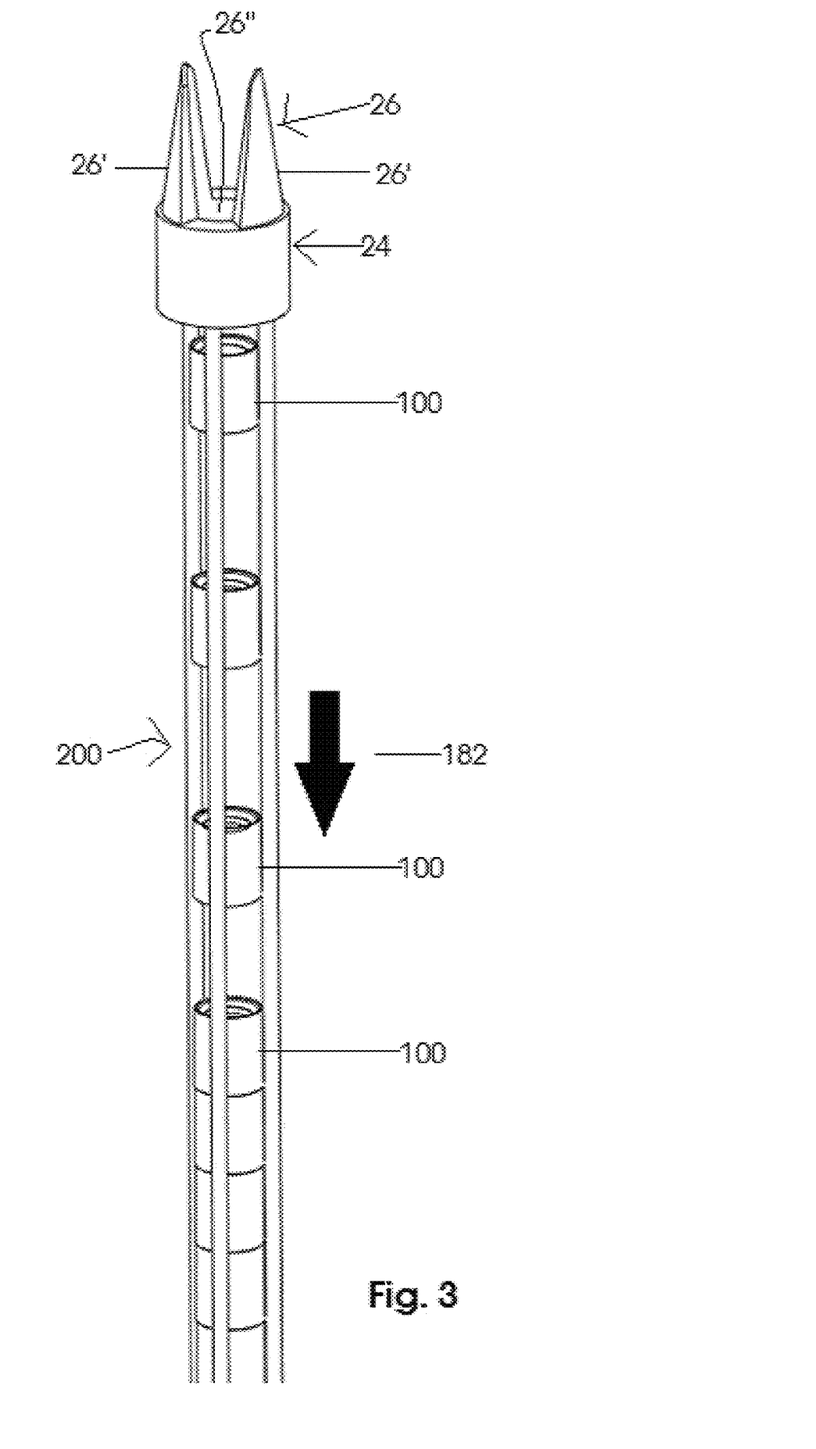
FIG. 3 is a perspective view of the access device being operatively attached in the interfacing orientation to the dispensing assembly concurrent to the passage of the contents from the package to the dispensing assembly.

With reference to the accompanying Figures and with initial reference to the embodiment represented in FIGS. 1-3, the system of the present invention incorporates the utilization of a package generally indicated as 10. The package 10 includes a base 12 secured in substantially surrounding relation to a chamber 14. In order to further restrict the possibility of physical touching or manual access to the plurality of products 100 within the chamber 14, the base 12 may be formed from an access resistant material, which resists manual tearing, ripping, etc. Such material can be multilayered and flexible, and secured by a fixed heat seal of the one or more layers of the base 12 to one another and to the chamber 14.

As indicated throughout FIGS. 1-3, the chamber 14 includes an elongated configuration, dimensioned and configured to retain a plurality of tamper evident closures and/or a "plurality of products" 100 within the interior of the chamber 14 in a substantially predetermined and aligned relation to one another. Due to the elongated and somewhat tubular configuration of the chamber 14, the predetermined aligned relation of the plurality of products 100 may be coaxially arranged in a column, as represented in FIG. 2A.

Still referring to FIGS. 1-3, additional structural features of the package 10 comprise a retaining structure generally indicated as 16, which will preferably be in the form of a removable or breakable seal 18. The retaining structure 16, including the removable seal 18, is disposed in retaining relation to the plurality of products 100 disposed within the chamber 14. The retaining structure 16 and/or removable seal 18 serves to at least initially segregate the plurality of products 100 from the exterior of the package 10 and/or base 12. The retaining structure 16 and/or removable seal 18 is preferably disposed within a recessed interior portion of the base 12, as represented throughout FIGS. 1-3. This recessed positioning of the retaining structure 16 is to prevent or at least significantly diminish the possibility of physically touching or other manual access to the interior of the chamber 14 by a user's hands, fingers, etc.

Therefore, the recessed interior portion of the base 12 is at least partially defined by a pocket 20 extending into the interior of the base 12 and including an open end 22, generally disposed along a peripheral portion of the base 12 in communicating relation with the exterior of the package 10. The system of the present invention intends to allow for the opening of the package 10 to facilitate the substantially automated dispensing of the plurality of products 100 from the interior of the chamber 14 to a delivery/processing assembly 200, as will be described in greater detail hereinafter.

Referring now to FIGS. 2A and 2B, the automated dispensing is facilitated by an access device, generally indicated as 24. The access device 24 includes a penetrating portion 26 which, in the embodiment of FIGS. 2A, 2B and 3, includes a substantially "forked" or bifurcated structure. Such a bifurcated structure may be defined by two spaced apart penetrating segments 26', disposed on opposite sides of an open interior of the access device 24. As such, the bifurcated penetrating portion 26 corresponds, at least in part to the overall configuration of the inner portion of the pocket 20 adjacent and/or contiguous to the removable seal 18 of the retaining structure 16.

Additional features of the access device 24 include a substantially open or hollow interior configuration. This open structuring of the access device 24 defines a "path of travel" best shown in FIG. 3 at 26" of the plurality of products 100 as they pass from the interior of the chamber 14 through the open structure of the access device 24 and are dispensed to the delivery/processing assembly 200. It should be further noted that the penetrating portion 26 of the access device 24, including the bifurcated segments 26' are disposed and configured to facilitate a channeling or directing of the plurality of products 100 from the interior of the chamber 14 into and through the open interior of the access device 24.

With reference again to FIGS. 2A, 2B and 3 the opening of the package 10 to provide access to the interior of the chamber 14 is accomplished by inserting the access device 24, including the penetrating portion 26, into the pocket 20 through the open end 22. The cooperative structures between the penetrating portion 26 and the interior of the pocket 20 facilitate the rupturing or breaking of the removable seal 18, as the package 10 and base 12 are forced into interacting engagement with the access device 24, as schematically represented by directional arrow 182.

Such interactive engagement between the access device 24 and the removable seal 18 will cause an opening of the chamber 14, through the rupturing of the removable seal 18 and a release of the plurality of products 100 therefrom. As indicated, the open structuring of the access device 20 defines the aforementioned "path of travel" 26" of the plurality of products 100 as they pass from the interior of the chamber 14, through the now open seal 18 and through the interior of the access device 24. Such continuous release or dispensing of the plurality of products 100 will occur under the influence of gravity, due to the vertical orientation as represented in at least FIGS. 2A and 2B. Moreover, such a gravity influence flow of the plurality of products 100 will be further enhanced by the access device 24 assuming and "interface orientation" as clearly represented in FIG. 2B and as indicated by directional arrow 182.

Therefore, one feature of the present invention is the structuring of the access device 24 to be disposed in the aforementioned "interface orientation" and thereby, in fact serving as an "interface" between the package 10 and the delivery/processing assembly 200. As represented in the successive procedural steps of FIGS. 2A and 2B, the interface orientation of the access device 24 includes it being disposed in interconnecting relation between the package 10 and the delivery/processing assembly 200, in a manner which aligns the base 12, chamber 14, access device 24 and delivery/processing assembly 200 in a substantially vertical alignment with one another. Due to the fact that the plurality of products 100 are substantially coaxially aligned and disposed in the aforementioned vertically oriented column, they will "automatically" pass, preferably under the influence of gravity, from the interior of the chamber 14, through the now open seal 18, through the path of travel 26" on the interior of the access device 24 and into the receiving portion of the delivery/processing assembly 200, as represented by directional arrow 182.

For purposes of clarity, it is emphasized that the delivery/processing assembly 200 is not considered a part of the system of the present invention and/or the structural components associated therewith. To the contrary, the delivery/processing 200 as schematically presented, is intended to represent one or more appropriate machines, devices, assemblies, facilities, etc. to which the plurality of products 100 may be dispensed utilizing the package 10 and the access device 24 according to one embodiment of the system of the present invention. Moreover, the access device 24 may be structurally modified, while still being defined within the intended spirit and scope of the present invention, to assume the interface orientation, represented in at least FIG. 2B. As such, the delivery/processing assembly 200 may assume a variety of different dimensions, configurations and overall structural features. However, it is assumed that each of the one or more possible delivery/processing assemblies 200, include structural and operative features which enable a substantially concurrent receiving of the plurality of products 100 as they pass successively, but rapidly, under the influence of gravity, from the interior of the chamber 14, through the path of travel 26" of the access device 24.

The versatility of the system of the present invention is enhanced by virtue of it being implemented utilizing different or structurally modified components, which have substantially common or equivalent operative features. Examples of such different or structurally modified components are represented in the additional embodiments shown in FIGS. 4-8. More specifically, the system of the present invention can be implemented utilizing a package 110 having a base 112. A chamber 114 is disposed on the interior of the base 112 and is also dimensioned and configured to arrange a plurality of components 100 in a substantially coaxially aligned, vertically oriented column, similar to that represented in the embodiment of FIG. 2A.

Figure 4:
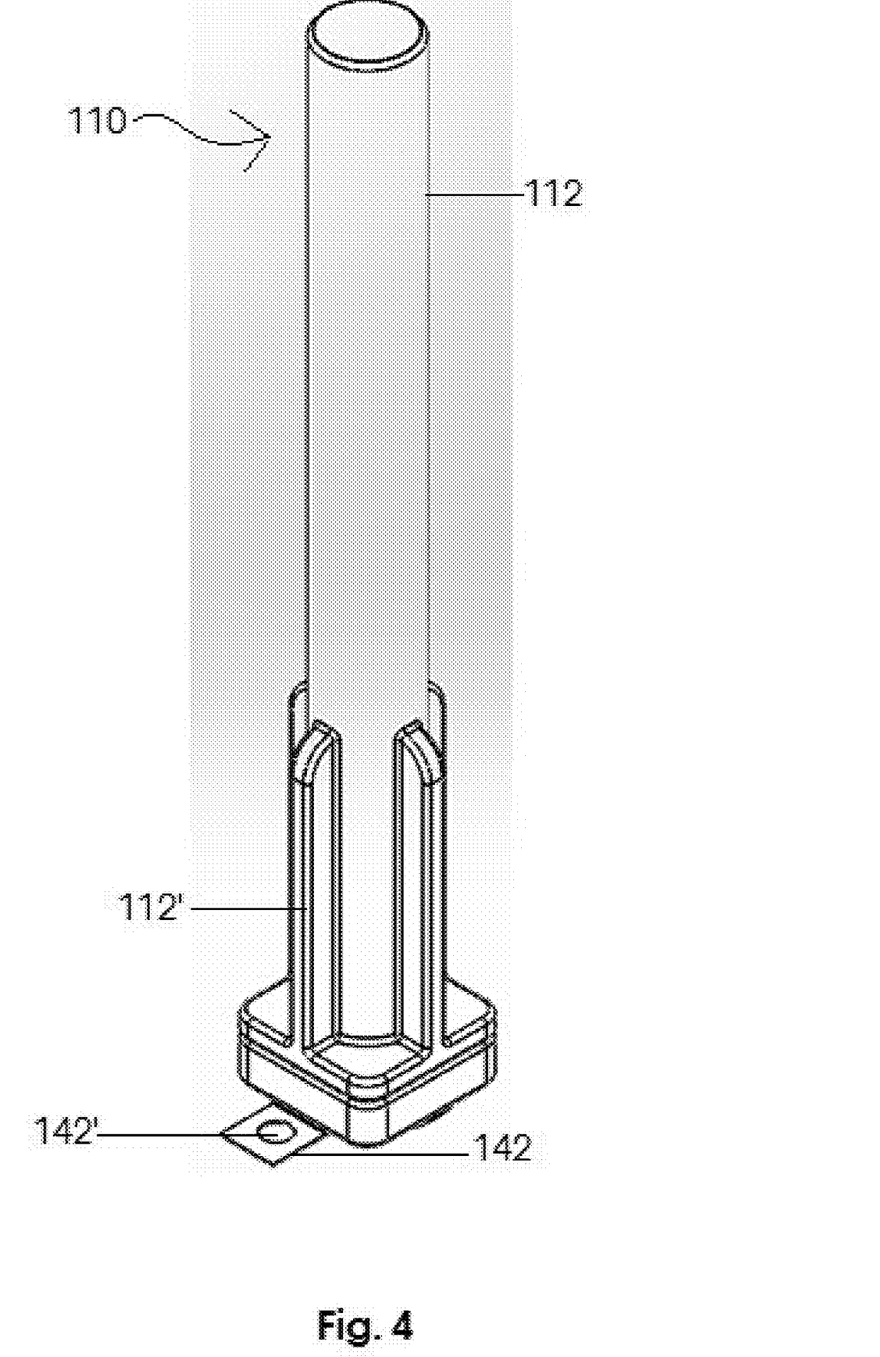
FIG. 4 is a perspective view of a package in another embodiment according to the present invention.

As can be noted from FIG. 4, the base 112 has a substantially tubular configuration and is formed from a relatively high strength, substantially rigid material, so as to be resistant to manual ripping, tearing, rupturing etc., which is disposed in surrounding relation to the interior chamber 114. As such, the rigid material of the base 112 will prohibit or at least significantly restrict physical touching or manual access to the interior of the chamber 114, as well as the plurality of components 100 initially retained therein. In addition, the base 112 includes a supporting platform or like structure 112' disposed at one end thereof. The support platform 112' is disposed, dimensioned and configured to maintain the package 110 in a substantially vertical, upright orientation as represented in FIG. 4.

Figure 6:
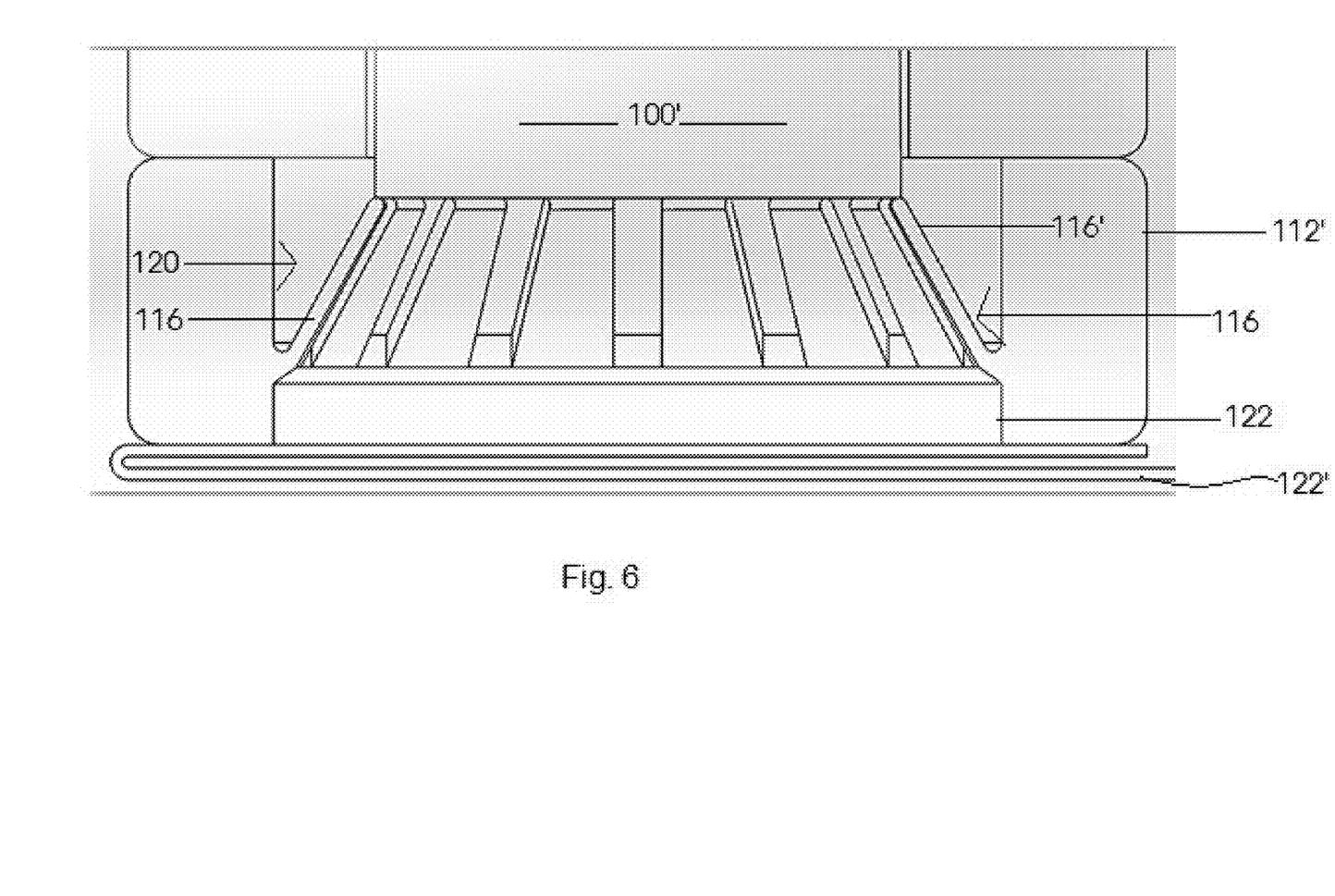
FIG. 6 is a detail interior sectional view of the package as represented in the embodiment of FIG. 5.

With reference to FIG. 6, the support platform 112' of the base 112 also includes a retaining structure generally indicated as 116. The retaining structure 116 is disposed within a recessed interior of the base 112 and more specifically, within the interior of a pocket 120 of the support platform 112'. The pocket 120 includes an open end 122, at least initially but removably closed by a cover member 122' as shown in FIG. 6.

Still referring to FIG. 6, the retaining structure 116 preferably comprises at least one, but possibly a plurality of flanges or like retaining segments 116'. The one or more retaining segments 116' are preferably formed of a flexible material, normally "biased" into retaining engagement with an end-most one of the plurality of products as at 100', represented in FIG. 6. Upon removal of the cover 122', as described hereinafter with reference to FIGS. 4 and 5, the interior of the pocket 120 will be exposed for access by an access device generally indicated as 124, shown in FIG. 7. The access device 124 is cooperatively structured with the package 110 to assume the "interface orientation" as at least partially represented in FIGS. 5-7.

Figure 5:
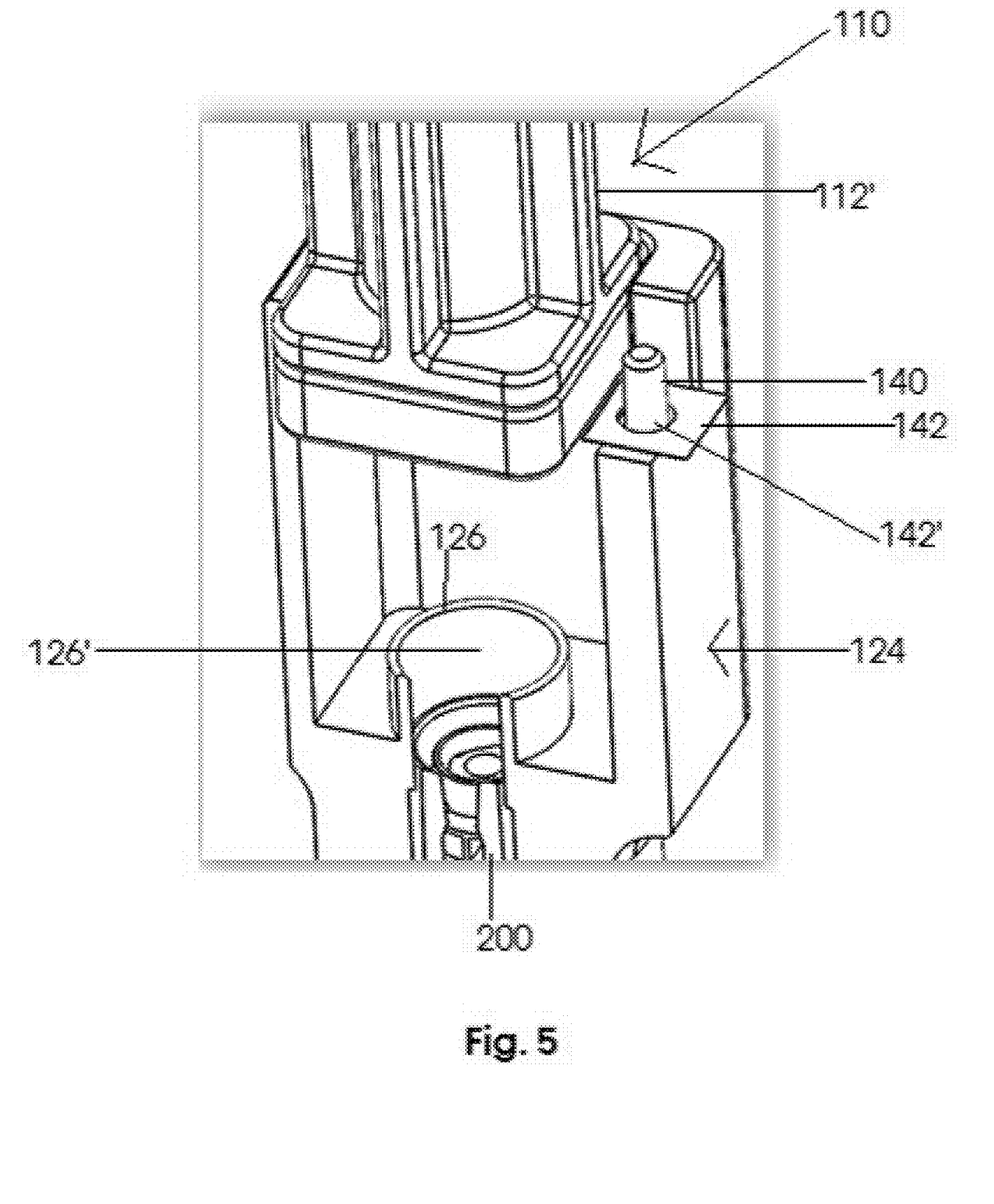
FIG. 5 is a perspective view in partial cutaway of the access device connected to the package of the embodiment of FIG. 4 and approaching disposition in an interface orientation.
Figure 7:
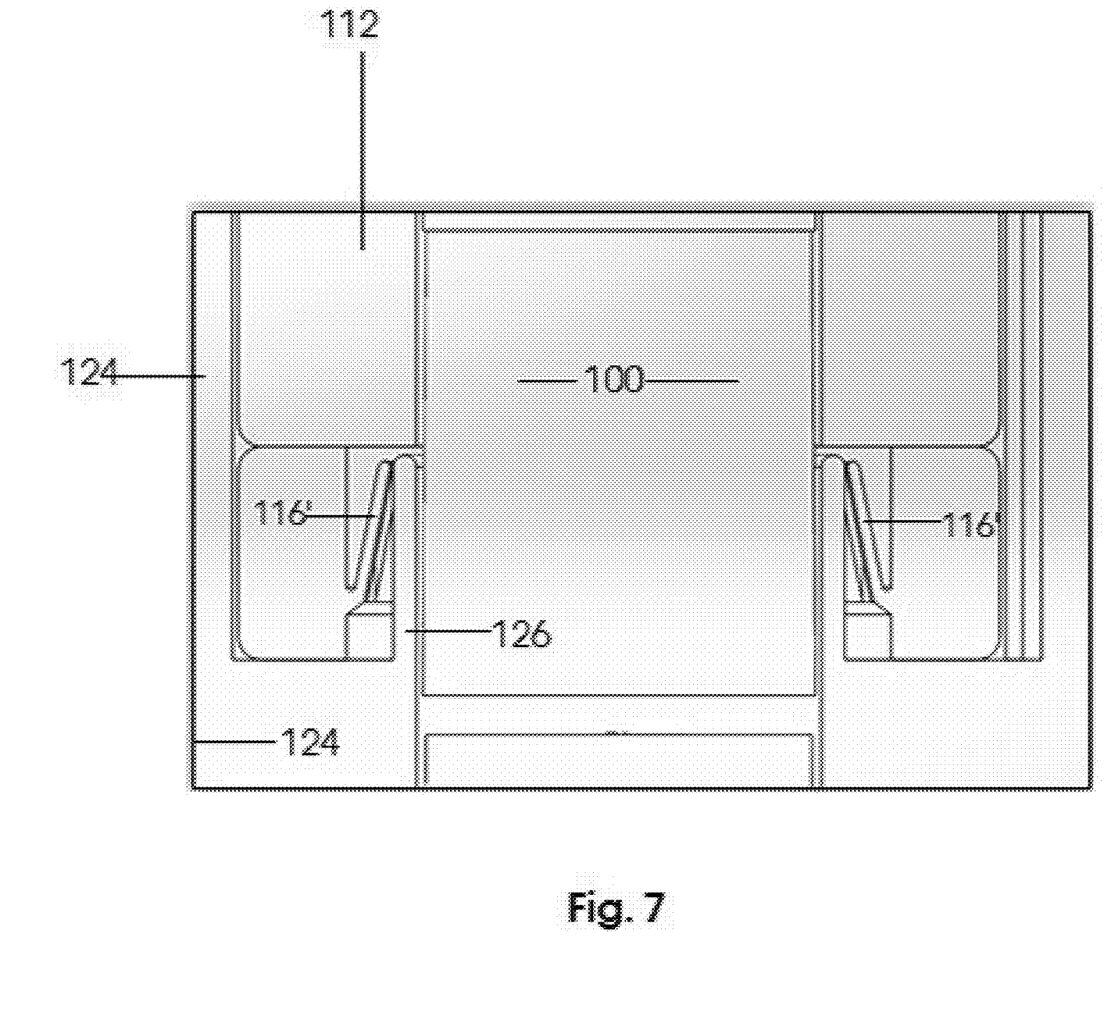
FIG. 7 is a detail interior sectional view of the embodiment of FIG. 6 wherein the access device is disposed in opening relation to the package concurrent to the removal of the contents of the package therefrom.

As shown in FIGS. 5 and 7, the access device 124 includes a penetrating portion 126 disposed, dimensioned and configured to enter the pocket 120 into opening engagement with the retaining structure 116 and more specifically, the one or more retaining segments or flanges 116', as clearly represented in FIG. 7. Also, the access device 124, including the area on the interior of the penetrating portion 126, is open and/or hollow and defines the aforementioned "path of travel", generally represented as 126'. Moreover, and as illustrated in FIG. 7, when the access device 124 is disposed in the interface orientation, the penetrating portion 126 will come into opening engagement with the retaining segments 116'. Such opening engagement will force or flex the one or more retaining segments 116' outwardly and away from retaining engagement within the end-most one 100' of the plurality of products 100. This opening engagement will open the interior of the chamber 114 and allow the plurality of products 100 to pass through the path of travel or open interior 126' of the access device/interface 124 through the penetrating portion 126, as also represented in FIG. 7.

The access device 124, when disposed in the interface orientation, will be disposed somewhat similar to that represented by the access device 24 in FIGS. 2A and 2B. More specifically, the access device 124 will be disposed in interconnecting relation between a vertically aligned package 110 and a delivery/processing assembly 200. This combined vertical orientation, concurrent to the opening of the chamber 114, will result in the gravity influenced, flow or passage of the plurality of products 100 from the interior of the chamber 114, through the open interior or path of travel 126' of the access device 124 and into and along a receiving or retaining portion of the delivery/processing assembly 200, to which the plurality of products 100 are automatically dispensed.

As should be apparent, opening of the interior of the chamber 114 further involves the removal of the aforementioned cover 122' from the open end 122 of the pocket 120. This is accomplished by the inclusion of a removing structure 140 formed on an appropriate portion of the access device 124, so as to be aligned with an outwardly extending tab 142 of the cover 122' such as is shown in FIG. 4. The tab 142 may include an aperture as at 142' also shown in FIG. 4. As the access device 124 engages and passes into the interior of the pocket 120, into the completed interface orientation, the removing structure 140 will pass through the aperture 142', in retaining engagement with the tab 142 and the cover 122'. A continued passage of the penetrating portion 126 into the interior of the pocket 120, as represented in FIG. 7, will result in the cover 122' being peeled away from the open end 122 of the pocket 120. The pocket 120 will thereby be opened for a clear and unobstructed insertion of the penetrating structure 126 into opening engagement with the retaining structure 116 and one or more retaining segments 116', as the access device 124 assumes the full interface orientation, as represented in FIG. 7.

Figure 8:
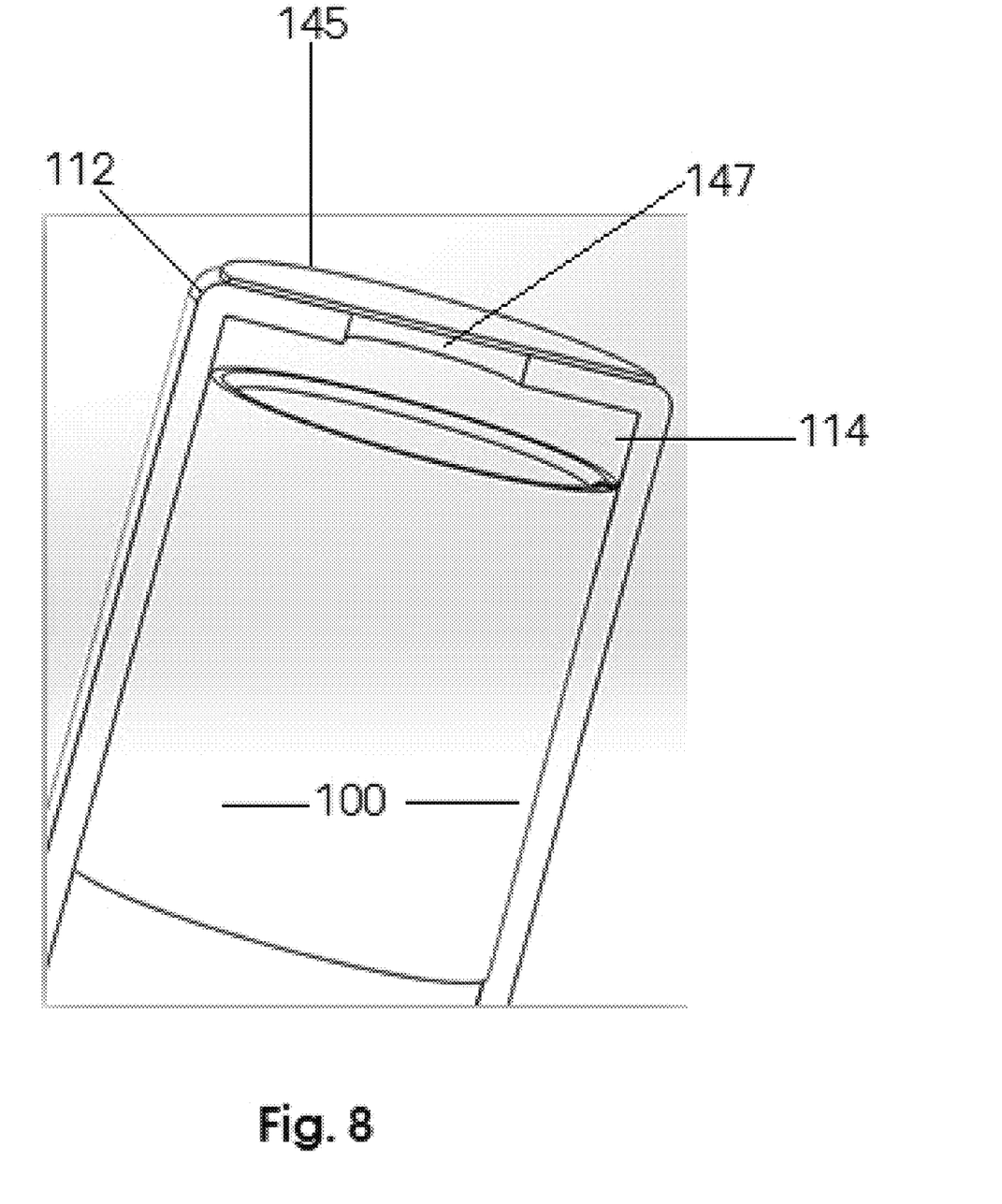
FIG. 8 is a detail view in partial cutaway of one end of the package of the embodiment of FIG. 4 including structure facilitating the sterilizing of the interior of the package and the plurality of products retained therein.

With reference now to FIG. 8, yet additional features of the embodiment of FIGS. 4-8 may include a membrane 145 disposed in overlying, covering relation to an opening or aperture 147 formed in an outer or distal end of the base 112. As represented FIG. 8, the aperture 147 is disposed in direct fluid communication with the interior of the chamber 14. Further, the membrane 145 is preferably formed from a gas permeable material, such as Tyvek®. As such, a sterilizing gas such as, but not limited to, ethylene trioxide may pass through the membrane 145 into the interior of the chamber 114, thereby serving to sterilize the plurality of products 100 contained therein.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A system for handling and dispensing a plurality of products, said system comprising:
   a package including a chamber configured to contain the plurality of products in a predetermined, aligned relation to one another,
   a base formed of rigid material disposed in surrounding relation to said chamber and including an interior pocket, including an open end,
   a retaining structure disposed on an interior of said pocket in removable retaining engagement with the plurality of products within said chamber,
   an access device structured for removable connection to said package in an interface orientation,
   said interface orientation comprising said access device removably disposed within said pocket into opening engagement with said retaining structure,
   said access device comprising an open interior disposed and dimensioned to define a path of travel of the plurality of products out of said chamber, and
   said package including at least one gas permeable structure disposed in fluid communication with an interior of said chamber and the plurality of products therein.

2. The system as recited in claim 1 wherein said interface orientation further comprises said access device removably connected to said package in interconnected relation between said package and a dispensing assembly.

3. The system as recited in claim 2 wherein said interface orientation further comprises said chamber, said path of travel and the plurality of products collectively being disposed in a vertical alignment with the dispensing assembly; said vertical alignment defining a gravity influenced passage of the plurality of products through said path of travel.

4. The system as recited in claim 1 wherein said chamber comprises an elongated configuration dimensioned to define said predetermined aligned relation of the plurality of products in a coaxially aligned column.

5. The system as recited in claim 1 further comprising a cover removably disposed in closing relation to said open end of said pocket; said access device including a removing structure disposed in removable engagement with said cover, substantially concurrent to said opening engagement of said access device with said retaining structure.

6. The system as recited in claim 1 wherein said base comprises an elongated, tubular configuration formed of the rigid material; said chamber disposed within said base and extending along the length thereof; said pocket formed within one end of said base and said retaining structure disposed within said pocket in retaining relation with the plurality of products, between said chamber and said open end of said pocket.

7. The system as recited in claim 6 wherein said retaining structure comprises at least one retaining segment removably biased into said retaining relation with the plurality of products.

8. The system as recited in claim 7 wherein said access device comprises a penetrating portion disposed into said opening engagement with said at least one retaining segment, concurrent to disposition of said access device in said interface orientation.

9. A system for handling and dispensing a plurality of products, said system comprising:
   a package including a chamber configured to contain the plurality of products in a predetermined, aligned relation to one another,
   a base formed of rigid material disposed in surrounding relation to said chamber and including an interior pocket having an open end, a retaining structure disposed on an interior of said pocket in removable retaining engagement with the plurality of products within said chamber, an access device comprising a penetrating portion and being structured for removable connection to said package in an interface orientation, said interface orientation comprising said penetrating portion of said access device removably disposed within said pocket, through said open end, in said opening engagement with said retaining structure, and said access device comprising an open interior disposed and dimensioned to define a path of travel of the plurality of products out of said chamber.

10. A system for handling and dispensing a plurality of products, said system comprising:
   a package including a chamber configured to contain the plurality of products in a predetermined, aligned relation to one another, a base comprising an elongated, tubular configuration formed of rigid material disposed in surrounding relation to said chamber and including an interior pocket formed within one end of said base, said chamber disposed within and extending along the length of said base;

a retaining structure disposed on an interior of said pocket in removable retaining engagement with the plurality of products within said chamber, said retaining structure disposed between said chamber and an open end of said pocket, an access device structured for removable connection to said package in an interface orientation, said interface orientation comprising said access device removably disposed within said pocket into opening engagement with said retaining structure, and said access device comprising an open interior disposed and dimensioned to define a path of travel of the plurality of products out of said chamber.

* * * * *